United States Patent [19]

Hamill et al.

[11] 3,952,095

[45] Apr. 20, 1976

[54] NOVEL ANTIBIOTIC AND A PROCESS FOR THE PRODUCTION THEREOF

[75] Inventors: Robert L. Hamill, New Ross; William M. Stark; Donald C. DeLong, both of Indianapolis, all of Ind.

[73] Assignee: Eli Lilly and Company, Indianapolis, Ind.

[22] Filed: Dec. 17, 1974

[21] Appl. No.: 533,570

Related U.S. Application Data

[63] Continuation-in-part of Ser. No. 259,334, June 2, 1972, abandoned, which is a continuation-in-part of Ser. No. 118,674, Feb. 25, 1971, abandoned.

[52] U.S. Cl. ................................................. 424/118
[51] Int. Cl.² ......................................... A61K 35/00
[58] Field of Search ...................................... 424/118

[56] References Cited

UNITED STATES PATENTS

| | | | |
|---|---|---|---|
| 3,632,749 | 1/1972 | Aszalos et al. | 424/118 |
| 3,639,582 | 2/1972 | Umezawa et al. | 424/118 |

*Primary Examiner*—Jerome D. Goldberg
*Attorney, Agent, or Firm*—Ralph W. Ernsberger; Everet F. Smith

[57] ABSTRACT

Antibiotic A-4696, produced by Actinoplanes sp., strain ATCC 23342, under submerged aerobic conditions in a liquid culture medium, isolated from the fermentation broth by adsorption on activated carbon, eluted therefom with a 1% sulfuric acid solution in acetone, and purified over sulfuric acid-washed alumina has antibacterial and growth promotant activity.

4 Claims, 1 Drawing Figure

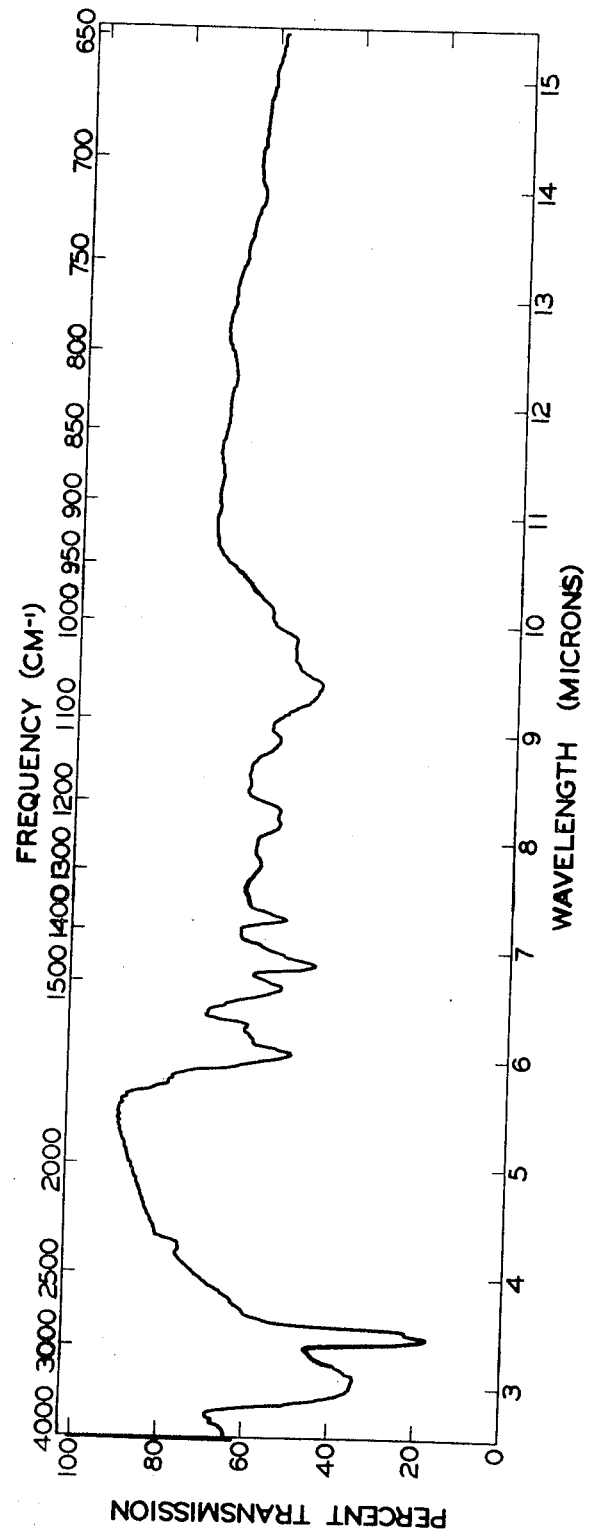
FIG. I

NOVEL ANTIBIOTIC AND A PROCESS FOR THE PRODUCTION THEREOF

CROSS-REFERENCE

This application is a continuation-in-part of co-pending application Ser. No. 259,334, filed June 2, 1972, now abandoned which was a continuation-in-part of application Ser. No. 118,674, filed Feb. 25, 1971, now abandoned.

BACKGROUND OF THE INVENTION

Tooth decay and gum disease are among the important health problems with which man is continuously struggling. The evidence is convincing that dentobacterial plaques are conducive to tooth caries, or periodontal lesions, or both. There is a need for prophylactic programs which will control the formation of dentobacterial plaque or keep such deposits below the level at which toxic reactions occur. Antibiotics which inhibit the growth of plaqueforming microorganisms have been developed, but there remains a need for more effective agents useful in the prevention and treatment of tooth decay and gum disease.

The efficient production of animal proteins for human consumption is a continuing problem in agriculture. Many agents have been found, among them numerous antibiotics, which are effective as feed additives in producing additional weight gain in growing chickens and swine. There is a never ending need for improved materials which are safe and economic and can be added to animal feed to increase the weight gain and to improve the feed efficiency. The discovery of agents which will accomplish this purpose represents a real advance in the art.

Summary

This invention relates to a novel antibiotic and to its preparation. More particularly, this invention relates to the novel nitrogenous antibiotic, arbitrarily denominated herein as A-4696.

The antibiotic of this invention is produced by culturing the organism Actinoplanes sp., strain ATCC 23342, in an aqueous nutrient medium under submerged aerobic fermentation conditions. The antibiotic is separated from the filtered fermentation broth by adsorption onto an activated adsorbent and eluted therefrom with an acidic solvent. Antibiotic A-4696 is purified as a crystalline compound by adsorption on an acidified chromatographic adsorbent and eluted therefrom with an acidic solvent. Preferably, the antibiotic is converted to the hydrochloride or sulfate salt in an aqueous methanol solution and obtained as a pure crystalline salt by adding acetone thereto and filtering off the precipitate that forms. Antibiotic A-4696 possesses antibacterial and growth promotant activity.

Detailed Description of the Preferred Embodiments

The novel antibiotic of this invention is a basic compound capable of forming salts with suitable acids. The characterization data presented below are for antibiotic A-4696 in the form of its hydrochloride salt. The antibiotic is conveniently isolated and characterized as the hydrochloride salt, although other pharmaceutically acceptable salts can be prepared by employing methods well-known in the art.

Antibiotic A-4696, as the hydrochloride salt, is a white crystalline compound with a melting point greater that 220°C. It is soluble in water, and insoluble in solvents such as methanol, acetone, ether, chloroform, pyridine, benzene, aliphatic hydrocarbons, and the like. It is very stable in solution over a pH range of from about 1.0 to about 10.0, at temperatures up to about 27° C.

Electrometric titration of A-4696 hydrochloride in water or in dimethylformamide:water (2:1) produces a curve approximating a straight line with a slope of about 0.14 from pH 6.0 to 13.0.

An average of several microanalyses has shown A-4696 hydrochloride to have approximately the following percent elemental composition: C, 51.33; H, 5.79; N, 5.46; O, 30.96; Cl 6.72 percent. The apparent molecular weight as determined by the vapor pressure osmotic method is 1158.

The specific rotation ($[\alpha]_D$), of A-4696 hydrochloride at 25° C. is $-42.3°$ (C=1, $H_2O$).

The ultraviolet absorption spectrum of A-4696 hydrochloride in acidic and neutral solutions shows a single absorption maximum at 276 m$\mu$., with an extinction coefficient, $E_{1\ cm.}$ 1% of 65.

The infrared absorption spectrum of A-4696 hydrochloride in a mineral oil mull is shown in FIG. 1 of the accompanying drawing. The observed distinguishable absorption maxima over the range 2.0 to 15.0 $\mu$. are as follows: 3.0, 5.8, 5.9, 6.03, 6.15, 6.28, 6.63, 6.85, 7.27, 7.75, 8.1, 8.25, 8.9, 9.4, 9.9, 10.1 microns.

The paper chromatographic profile of A-4696 hydrochloride is $R_{bu\ the\ Rf}$ values in Table I, below. The values were obtained in each instance using Whatman No. 1 paper and the indicated solvent system. The location of the antibiotic on the chromatogram was determined by bioautograph using Bacillus subtilis as the organism.

TABLE I

| Paper Chromatography of A-4696 Hydrochloride | |
|---|---|
| Solvent Systems | $R_f$ Value* |
| 1 | 0.88 |
| 2 | 0.72 |
| 3 | 0.80 |
| 4 | 0.59 |
| 5 | 0.35 |
| 6 | 0.77 |
| 7 | 0.80 |
| 8 | 0.74 |
| 9 | 0.87 |
| 10 | 0.59 |
| 11 | 0.77 |

*$R_f$ value is defined as the ratio of the distance traveled by the antibiotic from the origin to the distance traveled by the solvent front from the origin.

Key to Solvent Systems:
1. Water saturated with butanol plus 1% p-toluenesulfonic acid.
2. Water saturated with methylisobutyl ketone plus 1% p-toluene-sulfonic acid.
3. Water saturated with methylisobutyl ketone plus 1% p-toluene-sulfonic acid and 1% piperidine.
4. Water:methanol:acetone (12:3:1). The solution is adjusted to pH 10.5 with $NH_4OH$ and then lowered to pH 7.5 with $H_3PO_4$.
5. Methanol:0.1N HCl (3:1).
6. One percent methylisobutyl ketone plus 0.5% $NH_4OH$ in water.
7. Seven percent sodium chloride plus 2.5% methylisobutyl ketone in water.
8. Ten percent propanol in water.
9. Butanol:ethanol:water (150:15:13.5).
10. Propanol:pyridine:acetic acid:water (15:10:3:12).
11. Water:ethanol:acetic acid (70:24:6).

It is believed that antibiotic A-4696 may be comprised of as many as five undelineated factors. When a sample of the antibiotic was subjected to a 16-hour development of a paper chromatographic system utilizing a 15:10:3:12 n-butanol, pyridine, acetic acid, water solution as a solvent, five discrete spots were observed. It was not possible to quantify the relative relationship between the spots and no structural distinctions could be made.

By employing methods well-known in the art, pharmaceutically acceptable salts of antibiotic A-4696 can be prepared with mineral acids such as hydrochloric, hydrobromic, sulfuric, phosphoric, and the like, and also with organic acids such as citric, tartaric, maleic, p-toluenesulfonic, salicylic, fumaric, acetic, propionic, and the like. The antibiotic salts of such acids can be prepared, for example, by acidifying a solution of the antibiotic free-base with the desired acid and precipitating the salt thusly formed by introducing ten volumes of acetone to the solution containing the A-4696 acid salt. The salts can likewise be prepared in certain instances by ion exchange on an ion exchange column. Other commonly used methods for the preparation of antibiotic salts can also be employed.

The novel antibiotic of this invention has an inhibiting action against the growth of many microbial organisms which are pathogenic to man, animals and plantlife, and is, therefore, useful in suppressing the growth of such organisms. The levels at which A-4696 hydrochloride shows inhibition against the growth of the illustrative organisms are set forth numerically in Table II, below. The inhibition levels were determined by either the agar-dilution test or the broth-dilution test, and are stated in terms of the minimum inhibitory concentration (MIC), micrograms(s) per milliliter (mcg./ml.). (Identified in Table II by the letter *ad* and *bd*, respectively).

In the agar-dilution test the test organism is streaked or implanted on agar plates containing various concentrations of A-4696 hydrochloride in the agar. The test plates are incubated at 37° C. for 48 hours, and the MIC is determined as the plate at the lowest concentration of the antibiotic where growth of the test organism is inhibited.

In the browth-dilution test a series of tubes containing nutrient broth and varying concentrations of A-4696 hydrochloride are inoculated with the test organism and incubated at 37° C. for 24 hours. The MIC is determined as the lowest antibiotic concentration where no growth is present in the tube.

TABLE II

| Test Organism | Minimum Inhibitory Concentration (mcg./ml.) | |
|---|---|---|
| Staphylococcus aureus 3055 | 12.5 | ad |
|  | 6.25 | bd |
| Bacillus subtilis | 0.78 | ad |
| Mycobacterium avium | 0.4 | ad |
| Streptococcus faecalis | 3.12 | ad |
| Trichophyton mentagrophytes | 0.2 | ad |
| Vibrio coli | 12.5 | bd |
| Mycoplasma gallisepticum | 50.0 | bd |
| Staphylococcus aureus (penicillin resistant) | 10.0 | bd |
| Staphylococcus aureus (methicillin resistant) | 5.0 | bd |
| Diplococcus pneumoniae | 3.12 | bd |
| Clostridium perfringens | 1.25 | bd |
| Clostridium tetani | 2.5 | bd |
| Corynebacterium gravis | 1.25 | bd |
| Lactobacillus casei | >100 | ad |

TABLE II-continued

| Test Organism | Minimum Inhibitory Concentration (mcg./ml.) | |
|---|---|---|
| Leuconostoc citrovorum | >100 | ad |
| Escherichia coli | >100 | ad |
| Proteus sp. | >100 | ad |
| Pseudomonas sp. | >100 | ad |
| Salmonella sp. | >100 | ad |
| Vibrio metschnikovii | >100 | ad |
| Saccharomyces pastorianus | >100 | ad |
| Candida albicans | >100 | ad |

Antibiotic A-4696 hydrochloride when given by subcutaneous injection to mice has in vivo antimicrobial activity against infectious organisms; for example: the $ED_{50}$ values (effective dose to protect 50% of the test animals) in illustrative infections are as follows when two doses are employed: Staphylococcus aureus, 9.2 mg./kg.; Streptococcus pyogenes, 0.68 mg./kg.; and Diplococcus pneumoniae, 0.76 mg./kg.

The novel antibiotic of this invention is also effective in inhibiting the growth of microorganisms which contribute to the development of periodontal disease and tooth decay. For example, a solution of A-4696 hydrochloride exhibits antimicrobial activity against plaque forming organisms as illustrated by the following test system: Tubes of nutrient broth containing 5% sucrose are inoculated with a cariogenic microorganism. Glass rods are immersed in the medium and the tubes are incubated at 37° C. overnight after which the layer of plaque (primarily cells and dextran) forms on the surface of the rods. The rods are then transferred to solutions containing varying concentrations of A-4696 hydrochloride and allowed to remain in contact with the antibiotic for 5, 10, and 15 minutes. After the appropriate time has elapsed, the rods are rinsed with sterile, deionized water, and immersed in uninoculated medium containing sucrose and bromthymol blue. After incubating overnight at 37° C., growth is detected by observing the color change from green to yellow due to the acid production of the organisms when grown in a sucrose containing medium.

A solution of A-4696 hydrochloride at a concentration of 0.01% was effective against an unidentified cariogenic Streptococcus sp. when in contact with the plaque encrusted rods for ten minutes. The growth of this organism was prevented by A-4696 hydrochloride at a 0.1% concentration when the solution was in contact with the test rod for 5 minutes.

Moreover, A-4696 hydrochlorde inhibits the growth of the plaque-forming organism Odontomyces viscosus at a concentration of 0.25 mcg./ml. in a broth-dilution test.

The incorporation of A-4696 or one of its acid addition salts into an appropriate toothpaste, gel, powder, or the like, or a suitable mouthwash, or other oral hygiene preparation, can provide an effective method for inhibiting the development of dental caries and periodontal disease. Alternatively, a solution of A-4696, or one of its acid addition salts at an appropriate concentration can be applied to the surface of the gums and teeth with a suitable swab.

Also, it has been found that the daily oral administration of a growth promoting quantity of antibiotic A-4696, or a suitable derivative thereof, as a component in the feed consumed by poultry and swine significantly accelerates the growth rate of the animals and improves the efficiency of feed utilization. The daily ingestion by poultry and swine of antibiotic A-4696 or a suitable derivative thereof in an amount of from about 0.5 mg. to about 25 mg./kg. of body weight results in a faster growth than that registered by animals fed the same basal ration without the active agent. For example, broiler cockerels ingesting about 2 mg./kg. of antibiotic A-4696 hydrochloride daily gained 4.35 percent more weight and consumed 3.29 percent less total feed from age 7 days to age 28 days than comparable cockerels eating the same basal ration. The term "basal ration" as used herein refers to the total feed intake of the animal, which may take the form of a complete feed ration into which are incorporated in one composition all of the elements constituting the dietary requirements of the animal, or may be regarded as the sum of all of the elements contained in various feedstuffs, concentrates, supplements, mineral, vitamin or medicated premixes, roughages, or the like, which are fed to the animal. The composition and analysis of a typical poultry basal ration fed as a complete feed is shown in Table III, below.

TABLE III

| INGREDIENTS | Broiler Basal Ratio PERCENT | LBS./TON |
|---|---|---|
| Corn, Yellow, Ground | 53.90 | 1078 |
| Soybean Oil Meal Sol. Ext. 50% | 29.00 | 580 |
| Distillers Dried Sol. (Corn) | 2.50 | 50 |
| Alfalfa Meal, Dehydrated 17% | 2.50 | 50 |
| Whey, Dried | 1.00 | 20 |
| Fish Meal (Menh) + Sol. | 4.00 | 80 |
| Animal Fat | 4.00 | 80 |
| Dicalcium Phosphate, Feed Grade | 1.70 | 34 |
| Calcium Carbonate | .50 | 10 |
| Salt (NaCl) | .30 | 6 |
| Trace Mineral Premix[1] | .10 | 2 |
| Vitamin Mix CK-01 (1.02)[2] | .50 | 10 |
| Methionine Hydroxy Analogue (80%) | .062 | 1.25 |
| Totals | 100.062 | 2001.25 |

[1]Trace Mineral Premix contains: 6.7% manganese as manganese sulfate, 0.09% iodine as potassium iodide, 0.17% copper as copper oxide, 7.5% zinc and zinc carbonate, and 1.7% iron as ferrous sulfate.
[2]Each pound contains: 450,000 I.U. vitamin A, 120,000 I.C.U. vitamin $D_3$, 1,000 I.U. vitamin E, 400 mg. riboflavin, 3,600 mg. niacin, 966 mg. d-panthothenic acid, 26,037 mg. choline, 1 mg. vitamin $B_{12}$ and 100 mg. menadione sodium bisulfite.

Moreover, pigs ingesting from about 1.25 to about 6 mg./kg./day antibiotic A-4696 hydrochloride gained about 5.7 percent more weight and consumed about 4.1 percent less feed per pound of weight gained from the time they weighted about 50 pounds until they reached slaughter weight at about 200 pounds than comparable pigs eating the same basal ration but without the active compound. The composition and analysis of a typical swine basal ration is shown in Table IV, below.

TABLE IV

| INGREDIENTS | Swine Basal Starter Ration PERCENT | LBS./TON |
|---|---|---|
| Corn, Yellow, Ground | 69.25 | 1385 |
| Alfalfa Meal, Dehydrated 17% | 2.50 | 50 |
| Soybean Oil Meal, Sovent Extracted Dehulled 50% | 17.00 | 340 |
| Meat Scraps, 55% | 2.50 | 50 |
| Fish Meal with Solubles | 2.50 | 50 |
| Distillers Dried Solubles (Corn) | 2.50 | 50 |
| Animal Fat | 2.00 | 40 |
| Salt (NaCl) | 0.50 | 10 |
| Dicalcium Phosphate, Feed Grade | 0.50 | 10 |
| Calcium Carbonate | 0.20 | 4 |
| Trace Mineral Premix[1] | 0.05 | 1 |
| Vitamin Premix - SW-03[2] | 0.05 | 10 |
| Totals | 100.00 | 2000 |

[1]Trace Mineral Premix contains: 10.00% manganese as manganese sulfate, 0.30% iodine as potassium iodide, 0.10% cobalt as cobalt carbonate, 6.00% iron as ferrous carbonate, 1.00% copper as copper oxide, 10.00% zinc as zinc oxide, and 11.50% maximum and 8.50% minimum calcium carbonate.
[2]Each pound contains: 35,000 USP units vitamin $D_3$, 200 mg. riboflavin, 1,000 mg. niacin, 735 mg. pantothenic acid, 8,700 mg. choline and 2 mg. vitamin $B_{12}$.

In a preferred embodiment of the present invention, antibiotic A-4696, or a suitable derivative thereof, is administered orally in a suitable feed in which the active compound is present in an amount of from about 2 to about 200 grams per ton of total feed, the exact concentration employed being that which is required to provide for the active agent when normal amounts of feed are consumed. The addition of the active compounds of this useful process of this invention to animal feed is preferably accomplished by preparing an appropriate feed premix containing from about 1 to about 100 grams of antibiotic A-4696, or a suitable derivative thereof, per pound of premix and incorporating the premix into the complete ration. Alternatively, an intermediate concentrate or feed supplement containing the active agent can be blended into the feed.

The preparation of an appropriate feed premix can be effected by grinding the active compounds utilized in the novel process of this invention to a powder and admixing with a suitable premix carrier. The term "suitable premix carrier" as used in this disclosure may refer to an edible feedstuff which constitutes a normal dietary ingredient of the animal, such as, alfalfa grits, solvent-extracted soybean feed, ground corn, and the like, or a combination of components of a feed ration, or a physiologically utilizable mineral or vitamin concentrate or supplement, or the like. Alternatively the term may refer to a bland non-irritating material which is acceptable by the animal, but which is not physiologically utilizable, as for example, ground corn cobs, exfoliated hydrobiotite, or the like. The premix so prepared is then admixed with whatever feed ration is being fed to the animals at the time of administering the active agents employed in this useful process of the present invention. The feed premix can be diluted first with a feed supplement or feed concentrate to a desired concentration of the active compound, and the medicated supplement or concentrate can either be fed concurrently with the remainder of the ration or mixed into the final feed.

An alternative procedure for preparing the premix comprises dispersing the active compound in a suitable vehicle such as an edible vegetable oil, an edible glyceride, or an edible glycol, and spraying such dispersion onto the premix carrier with suitable mixing.

This aspect of the present invention is further illustrated by the following examples.

EXAMPLE 1

This test was run to compare weight gains and feed efficiencies in young broiler chickens when antibiotic A-4696 hydrochloride was fed in an amount of 45.4 grams of active compound per ton of basal ration with those observed when the basal ration with no growth promotant included therein was employed.

Sixty battery pens of 10 chicks each were utilized. The birds were one to five-day old broiler chicks (Arbor Acres Strain 50) at the start of the test. All of the birds were provided with the same basal ration (Table III, above) for the duration of the test. Thirty pens, a total of 300 birds, were provided with the basal ration without a growth promotant. Thirty pens, a total of 300 birds, were provided with the same ration containing, in addition, antibiotic A-4696 hydrochloride at a level of 45.4 grams per ton. The chicks were randomly assigned to the pens, and the test was conducted in a climate-controlled environment for either 10 or 17-day periods. Continuous lights and ad libitum feeding were used throughout the trials.

All birds were group weighed at the beginning and end of the trials. Average weight gains and feed efficiency were calculated for the period of the test.

The birds fed antibiotic A-4696 for 17 days produced a 6.06 percent greater weight gain and showed a 6.45 percent improvement in feed efficiency over the birds receiving no growth promotant.

Table V shows the test results.

birds were in housed in a temperature controlled environment and provided with ad libitum feeding and continuous lights. All of the chicks were fed the same chick starter ration (Table III, above) during the first 21 days of the test, and, in the case of the floor-pen trials, the same finisher ration (Table VI, below) during the remainder of the test.

The birds in the 21-day battery trial showed statistically significant improvement in weight gain at the 5, 10, and 20 g. ton level. There were statistically significant improvements in weight gain and feed efficiency in the chickens in the 28-day floor-pen trial at the 20 g./ton level.

The results of the test are shown in Table VII.

TABLE V

Weight Gains and Feed Efficiency in Young Chicks Fed A-4696 Hydrochloride in the Feed Ration.

| Feed Ration | A-4696 Hydrochloride g./ton of Feed | No. of Days on Treatment | No. of Birds in Treatment | Average Gain, g./Bird | Feed Conversion Efficiency LB. Feed/LB. Gain |
|---|---|---|---|---|---|
| Basal ration | 0 | 10 | 40 | 147 | 1.53 |
| Basal ration plus A-4696 Hydrochloride | 45.4 | 10 | 40 | 146 | 1.47 |
| Basal ration | 0 | 10 | 20 | 146 | 1.50 |
| Basal ration plus A-4696 Hydrochloride | 45.4 | 10 | 20 | 153 | 1.45 |
| Basal ration | 0 | 17 | 80 | 295 | 1.56 |
| Basal ration plus A-4696 Hydrochloride | 45.4 | 17 | 80 | 320 | 1.46 |
| Basal ration | 0 | 17 | 80 | 300 | 1.51 |
| Basal ration plus A-4696 Hydrochloride | 45.4 | 17 | 80 | 318 | 1.43 |
| Basal ration | 0 | 17 | 80 | 287 | 1.58 |
| Basal ration plus A-4696 Hydrochloride | 45.4 | 17 | 80 | 307 | 1.47 |

EXAMPLE 2

This test was run to compare weight gains and feed efficiencies when antibiotic A-4696 hydrochloride was fed in varying amounts and for different periods of time. Battery trials were run at concentrations of 1, 5, 10, and 20 grams of active compound per ton of basal ration for 21 days (7–28 days of age). Floor-pen trials were run at concentrations of 5 and 20 grams of active compound per ton of basal ration for 28 and 56 days (7–35 and 7–63 days of age, respectively).

The battery trials were run with 8 birds in each pen. The floor-pen trials had 50 birds in each pen. All of the

TABLE VI

| | Broiler Finisher Ration | |
|---|---|---|
| INGREDIENTS | PERCENT | LBS./TON |
| Corn, Yellow, Ground | 65.8 | 1316 |
| Soybean Oil Meal Sol. Ext. (50%) | 26.4 | 528 |
| Animal Fat | 3.90 | 78.0 |
| Dicalcium Phosphate, Feed Grade | 2.30 | 46.0 |
| Calcium Carbonate | .70 | 14.0 |
| Salt (NaCl) | .40 | 8.0 |
| Trace Mineral Premix[1] | .10 | 2.0 |
| Vitamin Mix CK-01 (1.02)[2] | .50 | 10.0 |
| Totals | 100.10 | 2002.0 |

[1]Trace Mineral Premix contains: 6.7% manganese as manganese sulfate, 0.09% iodine as potassium iodide, 0.17% copper as copper oxide, 7.5% zinc and zinc carbonate, and 1.7% iron as ferrous sulfate.
[2]Each pound contains: 450,000 I.U. vitamin A, 120,000 I.C.U. vitamin $D_3$, 1,000 I.U. vitamin E, 400 mg. riboflavin, 3,600 mg. niacin, 966 mg. d-panthothenic acid 26,037 mg. choline, 1 mg. vitamin $B_{12}$ and 100 mg. menadione sodium bisulfite.

TABLE VII

Weight Gains and Feed Efficiency in Young Chickens Fed A-4696 Hydrochloride in the Feed Ration

| Type of Trial | Feed Ration | A-4696 Hydrochloride g./ton of Feed | No. of Days on treatment | No. of Chickens in Treatment | Average Gain g./Chicken | % Improvement | Feed Conversion Efficiency Feed/lb. Gain | % Improvement |
|---|---|---|---|---|---|---|---|---|
| Battery | Basal Ration | 0 | 21 | 656 | 537.5 | — | 1.694 | — |
| do. | Basal Ration plus A-4696 Hydrochloride | 1 | 21 | 192 | 536.5 | −0.19 | 1.686 | 0.47 |
| do. | do. | 5 | 21 | 192 | 553.0 | 2.88 | 1.639* | 3.36 |
| do. | do. | 10 | 21 | 192 | 5559.1* | 4.02 | 1.648* | 2.79 |
| do. | do. | 20 | 21 | 384 | 560.9* | 4.35 | 1.640* | 3.29 |
| Floor-Pen | Basal Ration | 0 | 28 | 900 | 550.7 | — | 1.794 | — |

TABLE VII-continued

Weight Gains and Feed Efficiency in Young Chickens Fed A-4696 Hydrochloride in the Feed Ration

| Type of Trial | Feed Ration | A-4696 Hydrochloride g./ton of Feed | No. of Days on treatment | No. of Chickens in Treatment | Average Gain g./Chicken | % Improvement | Feed Conversion Efficiency Feed/lb. Gain | % Improvement |
|---|---|---|---|---|---|---|---|---|
| do. | Basal Ration plus A-4696 Hydrochloride | 5 | 28 | 300 | 570.3 | 3.56 | 1.727 | 3.88 |
| do. | do. | 20 | 28 | 900 | 582.9* | 5.85 | 1.704* | 5.28 |
| Floor-Pen | Basal Ration | 0 | 56 | 300 | 1774 | — | 2.22 | — |
| do. | Basal Ration Plus A-4696 Hydrochloride | 5 | 56 | 300 | 1810 | 1.02 | 2.17 | 2.30 |
| do. | do. | 20 | 56 | 300 | 1822 | 2.70 | 2.16 | 2.77 |

*Statistically significant, $P < 0.05$

EXAMPLE 3

This test was run to determine the effect of feeding antibiotic A-4696 hydrochloride to weanling pigs and its influence on the average daily weight gain and feed efficiency was tested.

Forty-four weanling pigs at 4 to 5 weeks of age were weighed and assigned to 4 experimental groups of 11 pigs each on the basis of weight and litter. Pigs were housed in enclosed buildings with adequate heat and ventilation, and feed and water were available ad libitum at all times. In each test the pigs were divided into two groups, one of the groups received the basal ration (Table IV, above) with no antibiotic added, and the other group received the same basal ration plus antibiotic A-4696 hydrochloride. Table VIII, shown below, lists the improvement in average daily gain and feed efficiency in those pigs which were fed the A-4696 hydrochloride as contrasted with those which received only the basal ration. The pigs getting feed containing 50 g./ton of A-4696 hydrochloride gained 11.8 percent more weight and had a 10.0 percent lower feed consumption than the control animals receiving no antibiotic.

TABLE VIII

Average Daily Weight Gain and Feed Efficiency in Weanling Pigs Fed Antibiotic A-4696 Hydrochloride as a Part of the Daily Diet

| Feed Ration | A-4696 Hydrochloride g./ton | No. of Pigs in Test | No. of Days on Test | Average Daily Gain Pounds | Feed Conversion Efficiency LB. Feed/LB. G |
|---|---|---|---|---|---|
| Basal ration | 0 | 11 | 28 | 0.67 | 1.91 |
| Basal ration plus A-4696 Hydro-Chloride | 20 | 11 | 28 | 0.95 | 1.77 |
| Basal ration | 0 | 11 | 34 | 1.10 | 2.41 |
| Basal ration plus A-4696 Hydro-Chloride | 50 | 11 | 34 | 1.23 | 2.17 |

EXAMPLE 4

This test was run to determine the effect of feeding antibiotic A-4696 hydrochloride to pigs from the time they are about 50 pounds each until they reach slaughter weight, (about 200 pounds).

Four groups of pigs, each numbering 72 animals, were housed in enclosed buildings with adequate heat and ventilation. Feed and water were available ad libitum. All pigs were fed a basal ration (Table IX, below) for two weeks before initiating the trials. One group of 72 pigs received no antibiotic for the duration of the test, and the other three groups were fed antibiotic A-4696 hydrochloride at levels of 4.54, 18.1 and 45.4 g./ton of feed. All animals received the same basal ration at all times.

The pigs fed antibiotic A-4696 hydrochloride at the 45.4 g./ton level gained 5.7 percent more weight and consumed 4.1 percent less feed than the control animals receiving no antibiotics.

The pertinent data generated in this test are nummarized in Table X, below.

TABLE IX

| SWINE GROWER RATION | | |
|---|---|---|
| Ingredient | Percent | Lbs./Ton |
| Corn, Yellow, Ground | 73.2 | 1464 |
| Alfalfa Meal, Dehydrated, 17% | 2.5 | 50 |
| Soybean Oil Meal, Solvent Extracted Dehulled, 50% | 12.6 | 246 |
| Meat Scraps, 55% | 2.5 | 50 |
| Fish Meal with Solubles | 2.5 | 50 |
| Distillers Dried Solubles (Corn) | 2.5 | 50 |
| Animal Fat | 2.0 | 40 |
| Calcium Carbonate | 0.7 | 14 |
| Dicalcium Phosphate, Feed Grade | 0.5 | 10 |
| Salt (NaCl) | 0.5 | 10 |
| Trace Mineral Premix, AN-03[1] | 0.1 | 2 |
| Swine Vitamin Premix, SW-03[2] | 0.5 | 10 |
| Methionine Hydroxy Analogue, 90% | 0.2 | 4 |
| Total | 100.3 | 2000 |

[1] Each kg. of premix contains the following: 50 gm of manganese sulfate, 100 gm. of zinc carbonate, 50 gm. of iron as ferrous sulfate, 5 gm. of copper as copper oxide, 1.5 gm. iodine as potassium iodide, and 150 gm. maximum and 130 gm. minimum calcium as calcium carbonate.

[2] Each kg. of premix contains the following: 77,161 USP units vitamin $D_3$; 440.0 mg. riboflavin; 2,240.6 mg. niacin; 1,602.4 mg. pantothenic acid; 19,180 mg. chlorine; 4.4 mg. vitamin $B_{12}$; 2000 mg. methyl testosterone, and 2000 mg. diethylstilbestrol.

TABLE X

Average Daily Weight Gain and Feed Conversion Efficiency in Pigs from 50 Pounds to About 200 Pounds Fed Antibiotic A-4696 Hydrochloride or a Part of the Daily Diet.

| Feed Ration | A-4696 Hydro-Chloride, PPM in Feed | No. of Pigs in Test | Weight of Pigs at Start of Test, LBS. Ave. | Weight of Pigs at Conclusion of Test, LBS. Ave. | Average Daily Gain Pounds | % Improvement | Feed Conversion Efficiency Lb. Feed/Lb. Gain | % Improvement |
|---|---|---|---|---|---|---|---|---|
| Basal Ration | 0 | 72 | 50 | 198.2 | 1.50 | — | 3.19 | — |
| Basal Ration Plus A-4696 Hydrochloride | 5 | 72 | 50 | 196.4 | 1.56 | — | 3.18 | — |
| do. | 20 | 72 | 50 | 197.1 | 1.57 | — | 3.07* | 3.8 |
| do. | 50 | 72 | 50 | 206.4 | 1.67* | 5.7 | 3.06* | 4.1 |

*Statistically significant ($P<.05$)

The acute toxicity of A-4696 hydrochloride, determined in mice and expressed as $LD_{50}$, is 2,400 mg./kg. when administered intraperitoneally.

The novel antibiotic of this invention is produced by culturing a newly discovered strain of an Actinoplanes organism under aerobic conditions in a suitable culture medium until the culture medium contains substantial antibiotic activity. The antibiotic can be recovered by employing various isolation and purification procedures commonly used and understood in the art. When the antibiotic is to be incorporated in feed-stuff for animal use, a lesser degree of purification is required than that which is necessary if the antibiotic is to be used for medicinal purposes.

The microorganism used according to this invention for the production of antibiotic A-4696 has been identified as a strain of a species of Actinoplanes of the family Actinoplanaceae. The Actinoplanaceae are a new family of microorganisms of the order Actinomycetales, having been first described by Dr. John N. Couch, Jour. Elisha Mitchell Sci. Soc., 65, 315–318 (1949); and 66, 87–92 (1950); Trans. New York Acad. Sci., 16, 315–318 (1954); Jour. Elisha Mitchell Sci. Soc., 71, 148–155 and 269 (1955); Bergey's Manual of Determinative Bacteriology, 7th Edition, 825–829 (1957); and Jour. Elisha Mitchell Sci. Soc., 79, 53–70 (1963).

The Actinoplanes sp. useful for the production of antibiotic A-4696 has been deposited and made a part of the stock culture collection of the American Type Culture Collection, Rockville, Md., from which it is available to the public without restriction under the number ATCC 23342.

The Actinoplanes sp. useful for the production of A-4696 was isolated from a sample of soil obtained from the Cascade mountain area in the state of Washington. This organism has been designated number 581 in the collection of Dr. John N. Couch at the University of North Carolina.

Actinoplanes sp., strain ATCC 23342, is characterized by the physical and cultural properties set forth in the following paragraphs. The system of Ridgeway, Color Standards and Nomenclature, (1912), is employed for the naming of the colors.

Microscopic Morphology and General Cultural Characteristics of Actinoplanes sp. ATCC 23342

Microscopic Morphology

Mycelia are rather sparse on Liquidamber (Sweet gum tree) pollen in water. The hyphae are branched, septate, 0.2–1.5$\mu$. in diameter. Hyphae fill the pollen grain, extending out in the water to a distance about equal to the diameter of the grain. Sporangiophores project above the surface of the water; sporangial stalks, usually single, at times branched to bear two, or rarely more, sporangia on the same sporangiophore; stalks 1.0–1.5$\mu$., thick, septate. Sporangia are rather small, 4–11$\mu$. in diameter, subglobose, rarely globose, usually with an irregular wall. Mature spores are arranged in one or more indistinct coils in the sporangium. Sporangial dehiscence is produced by the swelling of an intersporal substance which causes the sporangium to enlarge and assume an almost smooth spherical shape. Spores are motile, about 1.0–1.5$\mu$., in diameter; globose to subglobose.

Cultural Characteristics on:

Czapek Agar (S. A. Waksman, The Actinomycetes, 1950). Growth is good; the point inoculum about 2 cms. in diameter after eight weeks. The central part is mound-like; the smear flattened and minutely bumpy. The color of the mycelia is a brilliant zinc orange; the agar is pale buff to distinctly yellowish. Sporangia are rarely formed.

Peptone Czapek Agar (5 g. of peptone substituted for 2 g. of sodium nitrate). Growth is similar to that observed on Czapek Agar, but furrows, ridges and bumps are more distinct than on Czapek Agar. No sporangia are formed.

As previously noted, Actinoplanes sp., strain ATCC 23342, can be grown in a culture medium to produce antibiotic A-4696. The culture medium can be any one of a number of different media. However, for economy in production, maximum yield, and ease of isolation of the antibiotic certain culture media are preferred. Thus, for example, starch is one of the preferred sources of carbohydrate, and soybean meal is one of the preferred nitrogen sources. Other carbohydrate sources which can be used include molasses, glucose, dextrin, glycerol, and the like. Nitrogen sources also include amino acid mixtures, peptones, and the like.

Nutrient inorganic salts to be incorporated in the culture media can include the customary salts capable of yielding sodium, potassium, ammonia, calcium, phosphate, chloride, sulfate, acetate, carbohydrate, and like ions. Additionally, sources of growth factors, such as distillers' solubles and yeast extracts, can be included with beneficial effect on the production of A-4696 antibiotic. As is necessary for the growth and development of other microorganisms, essential trace elements should also be included in the culture medium for growing the Actinoplanes sp. employed in this invention. Such trace elements are commonly supplied as impurities incidental to the addition of the other constituents of the medium.

The organism used to produce A-4696 can be grown over a relatively wide pH range. However, it is desirable to adjust the pH of the culture medium to between about the pH 6.5 and pH 7.2 before inoculation with the organism. As with other Actinomycetes, the pH of the growing medium gradually changes during the growth period; the pH at the end of the fermentation period usually ranging from about 7.0 to 7.8.

Submerged aerobic cultural conditions are preferred for the production of A-4696. Relatively small amounts of the antibiotic can be produced by shake flask culture; however, for the preparation of large amounts, submerged aerobic culture in sterile tanks is preferred. The culture medium in the sterile tank can be inoculated with a sporulated or mycelia frament suspension; but because of the time lag experienced when a sporulated suspension is used, the preferred inoculum is the vegetative form of the culture. More efficient use of fermentation equipment is realized by avoiding the time lag in the growth cycle.

Accordingly, it is desirable to produce a vegetative inoculum of the organism by inoculating a relatively small quantity of culture medium with the spores or mycelial fragments of the organism, and when a young active vegetative inoculum is obtained aseptically transfer it to the large tank. The medium in which the vegetative inoculum is grown can be the same as that utilized for largescale fermentation of A-4696, although other media can be employed.

The A-4696 producing Actinoplanes sp., strain ATCC 23342, grows at temperatures between about 20° and 40° C. The largest amounts of A-4696 appear to be produced at a temperature of about 30° C.

Sterile air is blown through the culture medium in the submerged aerobic culture process. The volume of air sparged into the culture medium varies from about 0.1 to about 1.0 volume of air per minute per volume of culture medium. The most efficient growth and antibiotic production are achieved when the volume of air is at least ½ volume of air per minute per volume of culture medium.

The rate of production of A-4696 and the concentration of antibiotic activity in the culture medium can be followed during the growth period by testing samples of the fermentation broth for antibiotic acitivity against organisms known to be susceptible to the antibiotic. One such assay organism useful in the present invention is *Bacillus subtilis*. The bioassay can be carried out by the standard turbidimetric or cup-plate methods, or by the paper disc assay on agar plates.

Generally, maximum production of the antibiotic occurs within about 4 to 6 days in shake flasks or submerged aerobic culture fermentations.

Antibiotic A-4696 can be recovered from the culture medium and separated from other substances which may be present by adsorptive and extractive techniques. Adsorptive techniques are preferred because such procedures avoid the use of large volumes of solvents required in extraction processes.

After fermentation, the antibiotic acitivity is present in both the broth and mycelium. The culture medium is filtered to separate the fermentation broth from the solid mycelia. The mycelial cake is washed with water and then slurried in water adjusted to a pH of 10.5 with 5.0N NaOH, agitated vigorously for 30 minutes and filtered. The two filtrates and the wash water are combined and the antibiotic activity adsorbed therefrom on a suitable adsorptive agent, such as activiated carbon, activated acid alumina, polyamide resin, cellulose, silica gel, and the like. The adsorption can be accomplished by passing the antibiotic activity-containing solution over a bed of the adsorbent, or by adding the adsorbent to the solution, mixing thoroughly for 20 to 30 minutes and filtering off the exhausted solvent. The antibiotic adhering to the adsorbent can be recovered as impure A-4696 by customary elution procedures.

The crude A-4696 can be purified by the preparation of the picrate salt and the conversion thereof to the hydrochloride salt, or by adsorption and elution procedures using an appropriate adsorbent or ion exchange resin. Suitable adsorbents include Polyamide resin (M. Woelm, Eschwege, Germany), acidic alumina, neutral alumina, basic alumina, silica gel, Amberlite XAD-2 (Rohm and Haas, Philadelphia), Amberlite XAD-4 (Rohm and Haas, Philadelphia), and Dowex 50 ($H^+$) (Dow Chemical, Midland, Michigan).

This invention is further illustrated by the following examples:

EXAMPLE 5

A. Shake Flask Fermentation of Antibiotic A-4696

Mycelial fragments of Actinoplanes sp., strain ATCC 23342 were inoculated on a nutrient agar slant having the following composition:

| Ingredient | Amount |
|---|---|
| Pre-cooked oatmeal | 60 g. |
| Yeast | 2.5 g. |
| $K_2HPO_4$ | 1.0 g. |
| Dried distiller's solubles | 5.0 g. |
| Czapek's mineral stock* | 5.0 ml. |
| Agar | 25 g. |
| Water, deionized | 1 l. |
| *Czapek's mineral stock has the following composition: | |
| KCl | 100 g. |
| $MgSO_4\ 7H_2O$ | 100 g. |
| $FeSO_4\ 7H_2O$ | 2 g. |
| (Dissolve in two mls. conc. HCl) | |
| Water, deionized | 1 l. |

The slant was inoculated with ATCC 23342 and incubated for 6 days at 30° C. The culture does not normally sporulate on this medium, and it is necessary to macerate the mycelial mat with a flattened, sharpened, inoculating needle in order to increase the number of potential growth centers. The macerated mature culture was covered with sterile distilled water and scraped carefully with a sterile rod to obtain a mycelial suspension.

The suspension thus obtained was used to inoculate 100 ml. of a sterile vegetative medium having the following composition:

| Ingredient | Amount |
|---|---|
| Glucose | 5.0 g. |
| Dextrin | 20.0 g. |
| Soybean meal | 15.0 g. |
| Yeast extract | 2.5 g. |
| Calcium carbonate | 1.0 g. |
| Water, tap | 1 l. |

The inoculated vegetative medium was grown for 48 hours at 30° C. on a rotary shaker operating at 250 rpm.

Ten ml. of the incubated vegetative medium was inoculated into 100 ml. of a sterile "bump" medium of the same composition as given next above. The thus inoculated "bump" medium was incubated for 24 hours at 30° C. with constant shaking on a rotary shaker operating at 250 rpm.

Four-tenths ml. of the incubated "bump" medium was inoculated into 100 ml. portions of a production medium of the composition shown below contained in 500 ml. Erlenmeyer flasks, and sterilized at 120° C. for 30 minutes:

| Ingredient | Percent |
| --- | --- |
| Dextrose | 1.0 |
| Dextrin | 3.0 |
| Peptone | 1.5 |
| Soybean meal | 0.5 |
| $MgSO_4 \cdot 7H_2O$ | 0.2 |
| Molasses, beet sugar | 1.5 |
| Corn steep liquor | 0.5 |
| Betaine | 0.1 |
| $K_2HPO_4$ | 0.05 |
| Water, deionized, q.s. | 25 l. |

The pH of the medium was adjusted to 7.5 with 5N sodium hydroxide solution before sterilization. After sterilization the pH was approximately 6.9.

The production fermentation was shaken for about 96 hours at a temperature of 30° C. on a rotary shaker operating at 250 rpm. The pH at the end of the fermentation cycle was about 7.2.

B. 40-liter tank fermentation of antibiotic A-4696

The preparation of the inoculum proceeded through the incubation of the "bump" medium detailed under section A, above 25 liters of a production medium as outlined above, with 0.02% Dow Corning antifoam added, was sterilized by autoclaving at 120° C. for 30 minutes and charged into a 40 l. fermentation tank. One-hundred milliliters of incubated "bump" medium was inoculated into the sterile production medium. The inoculated production medium contained in the 40 l. tank was allowed to ferment for 4 days at 30° C. The fermentation was aerated with sterile air in an amount of about one-half volume of air per volume of culture medium per minute. The fermenting production medium was agitated with a mixer utilizing an impeller of a proper size and turning at an appropriate rpm to insure adequate mixing of air with the medium. The pH of the culture medium gradually increased from an initial level of about 6.9 to about 7.2 as the fermentation proceeded.

C. Isolation of Antibiotic A-4696

The whole broth obtained from an A-4696 fermentation, as described above, was filtered with the aid of a commercial filter aid. The filtrate was set aside. The mycelial cake was washed with 32 l. of water and the wash water set aside. The mycelial cake was then suspended in an additional 32 l. of water and the pH of the mixture adjusted to pH 10.5 with 5N sodium hydroxide solution. The mycelial cake water suspension was stirred for 45 minutes and the mixture was filtered. This filtrate and the water wash were combined with the original filtrate from the fermentation broth and the pH of combined filtrates was adjusted to pH 4.0 with $H_2SO_4$. The acidified combined filtrates was passed through a carbon column utilizing 1 kg. of activated carbon, (Pittsburgh, 12 × 40). The activated carbon column was washed until the effluent was colorless. The A-4696 activity was adsorbed on the carbon column. The A-4696 activity was eluted from the carbon column utilizing a 1% $H_2SO_4$ solution in acetone: $H_2O$ (1:1). Two liters of the acidified acetone-water solution was sufficient to elute the A-4696 activity from the carbon column. The eluate containing the A-4696 activity was treated with a saturated barium hydroxide solution, in order to form a precipitate of barium sulfate, thus removing the sulfate ions from the solution.

The mixture was filtered and the barium sulfate precipitate was discarded. The filtrate containing the A-4696 activity was concentrated under vacuum to dryness. The resulting residue comprising the A-4696 activity amounted to approximately 80 g.

D. Conversion of A-4696 Activity to Crude A-4696 Hydrochloride.

The approximately 80 g. of A-4696 activity was taken up in a volume of 5 l. of water, and then treated with 500 g. of activated carbon (Darco G-60, Atlas Chemical, Wilmington, Del.) This mixture was stirred for 1 hour and then filtered. The filtrate was discarded. The carbon filter cake containing the A-4696 activity was washed with 1 l. of water and the water wash was discarded. The carbon filter cake was further washed with 1 l. of 0.05N aqueous hydrochloric acid. The acid wash was discarded. The washed carbon cake was eluted by stirring 30 minutes with 500 ml. of an aqueous hydrochloric acidacetone solution (0.05N HCl:acetone[7:3]). The mixture was filtered and the filtrate set aside. The elution of the activated carbon was repeated 4 times in the same manner, each time setting aside the filtrate. The five eluates containing the A-4696 activity were combined. The combined eluates were then concentrated under vacuum to a volume of approximately 100 ml. Two-hundred milliliters of methanol was added to the aqueous concentrate containing the A-4696 activity. Two liters of acetone was added to this aqueous-methanol aolution. A precipitate, consisting of crude A-4696 hydrochloride, formed in the acetone-aqueous methanol solution. After filtering and drying the precipitate, 60.9 g., of crude A-4696 hydrochloride was recovered.

E. Preparation of Crystalline A-4696 Hydrochloride

Twenty-five grams of A-4696 hydrochloride, prepared according to the procedure outlined in section D of this example, was dissolved in 20 ml. of water. The A-4696 hydrochloride solution was passed over a water washed Polyamide resin bed, (M. Woelm, Eschwege, Germany), contained in a glass column of approximately 7 × 60 centimeters. The effluent was set aside. The Polyamide resin column was washed with water at a flow rate of approximately 8-10 ml. per minute. The antimicrobial activity of the column effluent was measured by conventional procedures. The effluents containing antimicrobial activity were combined and concentrated to dryness under vacuum. The residue was dissolved in a mixture of 25 ml. water and 50 ml. methanol. This aqueous methanol solution of A-4696 hydrochloride was acidified to a pH of 2.0 with 5N HCl. Approximately 1.5 l. of acetone was added to the aqueous methanol solution to precipitate the hydrochloride salt recovered therefrom.

The filter cake containing the A-4696 hydrochloride was dissolved in minimum quantity of water. An amount of ethanol equal to twice the volume of water was then added and the mixture was heated to approximately 60° C. The mixture was then cooled and the hydrochloride salt of A-4696 crystallized therefrom.

The crystals were filtered and dried. Approximately 9 g. of crystalline A-4696 hydrochloride was recovered.

EXAMPLE 6

Purification of A-4696 Over Acid-washed Alumina

Two and three-tenths grams of crude A-4696, obtained as described in Example 1 through section D above, was dissolved in 20 ml. of 50 percent aqueous methanol and run over a 2 × 4 cm. column of acid-washed alumina (Alcoa). The column was immediately washed with methanol. The activity was eluted from the acid alumina with 50% aqueous methanol. Aliquots of the elution were collected and the antimicrobial activity determined on each fraction. The fractions which exhibited antimicrobial activity were combined, concentrated to approximately 100 ml. and acetone added to precipitate the A-4696. The precipitate was filtered and dried in vacuo, yielding approximately 930 mg. of pure crystalline A-4696.

The acid-washed alumina used in the purification described above was prepared as follows: Alcoa activiated alumina F-20 was washed with water adjusted to pH 3 with $H_2SO_4$ by stirring for 6 hours maintaining the pH at 3.0. The alumina was filtered off, washed with 50% aqueous methanol, and dried in an oven at 100° C.

EXAMPLE 7

Purification of A-4696 by the Preparation of the Picrate Salt and Conversion thereof to the Hydrochloride Salt.

Five-hundred milligrams of crude A-4696, obtained as described in Example 1 through section D above, was dissolved in 25 ml. of water and 25 ml. of a saturated aqueous solution of picric acid were added with stirring. The mixture was allowed to stand overnight at 5° C. and a precipitate formed. The precipitate was centrifuged off and dried. The precipitate thus obtained was dissolved in 25 ml. methanol, the pH was adjusted to 1.5 with HCl, and added to 500 ml. of diethyl ether to precipitate the A-4696 hydrochloride salt. The hydrochloride salt was centrifuged off, washed with diethyl ether and dried in vacuo yielding approximately 305 mg. of A-4696 hydrocloride as a whit crystalline salt.

EXAMPLE 8

Preparation of A-4696 Sulfate Salt

Two grams of A-4696 hydrochloride, obtained as described in Example 1 through section E above, was dissolved in 300 ml. of water, the pH adjusted to 7.5 with 5N sodium hydroxide, and 30 g. of Darco G-60 carbon was added. The mixture was stirred for 30 minutes; filtered with the aid of a commercial filter aid, and the filter cake washed successively with 300 ml. each of water and 0.05N $H_2SO_4$.

The activity was eluted from the filter cake by adding the filter cake to 500 ml. of a mixture consisting of 70% 0.05N $H_2SO_4$ and 30% acetone, stirring for 30 minutes and filtering to remove the carbon. The filtrate was concentrated to approximately 10 milliliters. About 20 ml. of methanol was added to the concentrate and the thus formed solution was added to 600 ml. of acetone to precipitate the A-4696 sultate. The precipitate was filtered off; washed with acetone and dried in vacuo, yielding 862 mg. of A-4696 sulfate as a white crystalline salt.

What is claimed is:

1. The antibiotic substance A-4696, or a pharmaceutically acceptable acid addition salt thereof, which antibiotic in the form of its hydrochloride salt is a white, crystalline substance soluble in water and insoluble in the common organic solvents, has a melting point greater than 220° C.; has an electrometric titration curve in 66 percent aqueous dimethylformamide approximating a straight line with a slope of about 0.14 from pH 6.0 to pH 13.0; has the approximate composition of 51.33 percent carbon, 5.79 percent hydrogen, 5.46 percent nitrogen, 30.96 percent oxygen, and 6.72 percent chlorine; has an apparent molecular weight of 1158, as determined by the vapor pressure osmotic method; had a specific rotation, $[\alpha]_D^{25}$ −42.3° (c=1, $H_2O$); has an ultraviolet absorption spectrum in acidic and neutral solutions at 276 m$\mu$. with an extinction coefficient $E_{1cm}.1\%$ of 65; and has the following distinguishable bands in its infrared absorption spectrum when determined in a mineral oil mull: 3.0, 5,8, 5.9, 6.03, 6.15, 6.28, 6.63, 6.85, 7.27, 7.75, 8.1, 8.25, 8.9, 9.4, 9.9, and 10.1 microns.

2. The hydrochloride salt of antibiotic A-4696 as defined in claim 1.

3. The sulfate salt of antibiotic A-4696 as defined in claim 1.

4. The method of producing the antibiotic of claim 1 which comprises cultivating the organism Actinoplanes sp., strain ATCC 23343, in an aqueous nutrient culture medium containing assimilable sources of carbon, nitrogen and inorganic salts under submerged aerobic fermentation conditions until a substantial amount of antibiotic activity is produced by said organism in said culture medium, and recovering said antibiotic from said culture medium by adsorbing said antibiotic on a suitable adsorptive agent and eluting said antibiotic therefrom.

\* \* \* \* \*